US00RE46228E

(19) United States
(12) Reissued Patent
Cebrián Puche et al.

(10) Patent Number: US RE46,228 E
(45) Date of Reissued Patent: Dec. 6, 2016

(54) PIGMENTATION-REGULATING COMPOUNDS

(71) Applicant: LIPOTEC, S.A., Gava (ES)

(72) Inventors: Juan Cebrián Puche, Barcelona (ES); Ángel Messeguer Peypoch, Barcelona (ES); Antonio Vicente Ferrer Montiel, Alicante (ES); Nuria Almiñana Doménech, Barcelona (ES); Cristina Carreño Serraïma, Barcelona (ES)

(73) Assignee: LIPOTEC, S.A., Gava, Barcelona (ES)

(21) Appl. No.: 14/175,312

(22) Filed: Feb. 7, 2014

Related U.S. Patent Documents

Reissue of:
(64) Patent No.: 8,110,207
Issued: Feb. 7, 2012
Appl. No.: 12/440,707
PCT Filed: Apr. 11, 2008
PCT No.: PCT/ES2008/000230
§ 371 (c)(1),
(2) Date: May 4, 2009
PCT Pub. No.: WO2008/152159
PCT Pub. Date: Dec. 18, 2008

U.S. Applications:
(60) Provisional application No. 61/037,085, filed on Mar. 17, 2008.

(30) Foreign Application Priority Data

Jun. 15, 2007 (ES) ..... 200701663

(51) Int. Cl.

| | |
|---|---|
| ***C07D 311/72*** | (2006.01) |
| ***C07D 409/12*** | (2006.01) |
| ***C07D 407/12*** | (2006.01) |
| ***C07D 405/12*** | (2006.01) |
| ***C07D 495/04*** | (2006.01) |
| ***A61Q 19/00*** | (2006.01) |
| ***A61Q 19/02*** | (2006.01) |
| ***A61K 8/49*** | (2006.01) |

(52) U.S. Cl.
CPC ..... *C07D 311/72* (2013.01); *C07D 495/04* (2013.01)

(58) Field of Classification Search
CPC ..... A61K 8/498; A61K 2800/78; A61Q 3/00; A61Q 19/00; A61Q 19/02; A61Q 19/04; C07D 495/04; C07D 311/72; C07D 405/12; C07D 407/12; C07D 409/12
USPC ..... 424/401, 400
See application file for complete search history.

(56) References Cited

U.S. PATENT DOCUMENTS

| | | | | |
|---|---|---|---|---|
| 5,605,703 | A * | 2/1997 | Lambiez | A61K 9/127 424/450 |
| 6,569,906 | B1 * | 5/2003 | Redoules et al. | 514/738 |
| 7,008,630 | B2 * | 3/2006 | Cals-Grierson et al. | 424/401 |
| 2003/0223982 | A1 | 12/2003 | Schlotmann et al. | |
| 2005/0238613 | A1 | 10/2005 | Cals-Grierson et al. | |

FOREIGN PATENT DOCUMENTS

| | | | |
|---|---|---|---|
| EP | 0655239 | A1 | 5/1995 |
| EP | 1002533 | A1 | 5/2000 |
| EP | 1 260 509 | A1 * | 11/2002 |
| EP | 1267813 | A2 | 1/2003 |
| EP | 1336403 | A1 | 8/2003 |
| EP | 1343465 | A2 | 9/2003 |
| EP | 1430879 | A2 | 6/2004 |
| EP | 1430933 | A2 | 6/2004 |
| EP | 1634576 | A1 | 3/2006 |
| EP | 1430882 | A2 | 4/2009 |
| JP | 52-147433 | A * | 12/1977 |
| JP | 2001-002558 | | 1/2001 |
| WO | WO 01/74320 | | 10/2001 |
| WO | WO 01/82888 | | 11/2001 |
| WO | WO 02/05778 | A1 | 1/2002 |

(Continued)

OTHER PUBLICATIONS

Puig A. Synthetic actives for cosmetic applications. Specialty Chemicals Magazine, 2002, 22(107):16-17.*
Silverman RB. The Organic Chemistry of Drug Design and Drug Action. Academic Press, Inc. 1992, pp. 352-356.*
Lipochroman-6. CODE:ES290. Skin cell damage prevention by RNS scavenging. Lipotec S.A. Feb. 2005.*
Boehnlein et al. Characterization of esterase and alcohol dehydrogenase activity in skin. Metabolism of retinyl palmitate to rentinol (vitamin A) during percutaneous absorption. Pharmaceutical Research, 1994, 11(8):1155-1159.*
Atherton, E., et al., "Solid Phase Peptide Synthesis: A practical approach," IRL Press Oxford University, UK, pp. 1-61 (1984).

(Continued)

*Primary Examiner* — Leslie A. Royds Draper
(74) *Attorney, Agent, or Firm* — Fay Sharpe LLP

(57) ABSTRACT

The present invention relates to compounds of general formula (I):

(I)

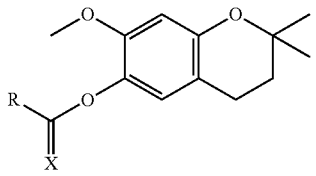

wherein X is selected from the group consisting of O or S and R is a linear or branched, saturated or unsaturated aliphatic group with from 2 to 23 carbon atoms ($C_2$ to $C_{23}$), or a cyclic group, and which can contain substituents selected from the group consisting of hydroxy, alkoxy, amino, carboxyl, cyano, nitro, alkylsulfonyl or halogen atoms, a method of obtaining them, cosmetic or pharmaceutical compositions containing them and the use thereof for treating, caring for and/or cleaning skin, hair and/or nails, preferably those conditions, disorders or pathologies of the skin, hair and/or nails which require regulating melanogenesis.

30 Claims, No Drawings

(56) References Cited

FOREIGN PATENT DOCUMENTS

| | | |
|---|---|---|
| WO | WO 02/47655 A1 | 6/2002 |
| WO | WO 02/49593 | 6/2002 |

OTHER PUBLICATIONS

Benmaman, O., et al., "Treatment and camouflaging of pigmentary disorders," Clin. Dermatol, pp. 50-61 (1988).
Berge, S. M., et al., "Pharmaceutical Salts," J. Pharm. Sci. 66, pp. 1-19 (1977).
Cebrián, J., et al., "New anti-RNS and -RCS products for cosmetic treatment," Int. J. Cosm. Science 27(5), pp. 271-278 (2005).
Dooley, T. P., "Recent advances in cutaneous melanoma oncogenesis research," Onco. Res. 6: pp. 1-9 (1994).
Dooley, T. P., "Is there room for a moderate level of regularity oversight?" in "Drug Discovery Approaches for Developing Cosmeceuticals: Advanced Skin Care and Cosmetic Products," Ed. Hori W, Chapter 1.4, International Business Communications, pp. 1.4.1-1.4.16(1997).
Dooley, T. P., "Topical skin depigmentation agents: Current products and discovery of novel inhibitors of melanogenesis," J. Dermatol. Treat. 8, pp. 275-279 (1997).
Fleisher, et al., "Improved oral drug delivery: solubility limitations overcome by the use of prodrugs," Advanced Drug Delivery Reviews, vol. 19, pp. 115-130 (1996).
Glatt, H., et al., "Multiple activation pathways of benzene leading to products with varying genotoxic characteristics," Environ. Health Perspect. 82, pp. 81-89 (1989).
Glatt, H. R., "Endogenous mutagens derived from amino acids," Mutat. Res. 238, pp. 235-243 (1990).
Greene, T. W., et al., in "Protective groups in organic synthesis", John Wiley & Sons, pp. 308-405 (1981).
Hearing, V.J., et al., "Enzymatic control of pigmentation in mammals," FASEB J. 5, pp. 2902-2909 (1991).
Hearing, V.J., "Biochemical control of melanogenesis and melanosomal organization," J. Invest. Dermatol. Symp. Proc. 4, pp. 24-28 (1999).
Kuwabara, Y., et al., "Topical Application of γ-Tocopherol Derivative Prevents UV-Induced Skin Pigmentation," Biol. Pharm. Bull, vol. 29(6), pp. 1175-1179 (2006).
Meredith, P., et al., "Radiative Relaxation Quantum Yields for Synthetic Eumelanin," Photochem. Photobiol. 79, pp. 211-216 (2004).
Nakagawa, M., et al., "Contact allergy to kojic acid in skin care products," Contact Dermatitis 42, pp. 9-13 (1995).
Nelson, G., "Application of microencapsulation in textiles," Int. J. Pharm. 242, pp. 55-62 (2002).
Piérard, G. E., et al., "Pigmentary changes in skin senescence," J. Appl. Cosmetol. 9, pp. 57-63 (1991).
Puig, A. "Synthetic actives for cosmetic applications," Specialty Chemicals Magazine 2002, 22(10), pp. 16-17 (2002).
Sanvicens, N., et al., "Oxidative stress-induced apoptosis in retinal photoreceptor cells is mediated by calpains and caspases and blocked by the oxygen radical scavenger CR-6," J. Biol. Chem. 279(38), pp. 39268-39278 (2004).
Schaab, C.K., "Impregnating Fabrics With Microcapsules" HAPPI, pp. 84-86 (May 1986.
Schallreuter, K. U., "Epidermal adrenergic signal transduction as part of the neuronal network in the human epidermis," J. Invest. Dermatol. 2, pp. 37-40 (1997).
Stefanaki, C., et al., "Topical retinoids in the treatment of photoaging," J. Cosmet. Dermatol. 4, pp. 130-134 (2005).
Wilkinson, J.B., et al., "Harry's Cosmetology," Longman Scientific & Technical, London, UK pp. 50-73, and 757-799 (1982).
Yenes, S., et al. "A Study of the Reaction of Difference Phenol Substrates with Nitric Oxide and Peroxynitrite," Tetrahedon, vol. 55, pp. 14111-14122 (1999).
International Search Report for PCT/ES2008/000230, dated Dec. 2, 2008.

* cited by examiner

PIGMENTATION-REGULATING COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This application claims the benefit of Spanish Patent Application P200701663, filed on Jun. 15, 2007, PCT/ES2008/000230, filed on Apr. 11, 2008, and U.S. 61/037,085, filed on Mar. 17, 2008.*

FIELD OF THE INVENTION

The present invention relates to 6-substituted 7-methoxy-2,2-dimethylchromanes and to cosmetic or pharmaceutical compositions containing these compounds for treating, caring for and/or cleaning skin, hair and/or nails, preferably for attenuating the degree of pigmentation of the skin and the hair or for treating spots on nails or for photoprotection of the skin, hair and nails.

BACKGROUND OF THE INVENTION

The modification of the natural pigmentation of the skin is a desirable fact for several reasons for many people in America, Asia or Europe. Some of the reasons for modifying the natural color of the skin include the search for lighter skin as a model of beauty, and the elimination or attenuation of spots on the skin such as freckles or lentigines.

Dysfunctions in the melanin production mechanism due to external aggressions, exposure to UV radiation, inflammations, hormonal disturbances, pregnancy (melasma), photoageing or ageing induce hyperpigmentation and the occurrence of brown spots, particularly in the form of freckles or solar or senile lentigines.

Skin and hair color is due to a series of cell processes carried out by melanocytes. Melanocytes are cells of neuroectodermal origin that are bound by dendrites to the cells of the basal layer of the epidermis at a proportion of approximately one melanocyte for every ten basal cells, regardless of race. The main function of the melanocyte is to synthesize the melanin through cellular and hormonal interaction.

Melanin is a dark pigment found in the skin, hair, eyes and certain nerve cells and protects the body from the harmful effects of ultraviolet radiation. There are two types of melanin pigments, eumelanin and pheomelanin. Eumelanin is black, while pheomelanin has a lighter color, between reddish and yellow. Skin and hair tone is determined by the proportion of one or another type of pigment. These pigments accumulate in melanosomes in the melanocyte cytoplasm and are carried by the melanosomes to dendrites where they are injected in the basal cell cytoplasm. A homogenous melanin distribution in the basal layer of the epidermis thus occurs, giving uniform pigmentation of the skin [Hearing V. J. (1999) "Biochemical control of melanogenesis and melanosomal organization" J. Invest. Dermatol. Symp. Proc. 4:24-28]. In the same manner, hair color depends on the amount and the quality of the melanin located in the cortex of the hair stalk. Said melanin is produced by the melanocytes located at the base of the root and depends on hereditary, hormonal, nutritional factors, etc. Over the years, the amount of melanin of the hair decreases due to the reduction of melanocyte activity, justifying the whitening of hair (gray hair).

Therefore, human skin and hair color is directly related to the size, configuration, type, color and distribution of these melanosomes. Melanosomes are formed by, among others, melanin and melanoprotein, which is a product of the interaction with the enzyme tyrosinase. Tyrosinase is a glycoprotein located in the membrane of melanosomes and catalyzes to first steps in formation of pigment, i.e. the ortho-hydroxylation of the amino acid tyrosine which produces L-dopa and the oxidation of the latter to give dopaquinone [Hearing V. G. and Tsukamoto K. (1991) "Enzymatic control of pigmentation in mammals" FASEB J. 5:2902-2909].

Depending on the levels of cysteine and/or of the compounds with sulfhydryl groups inside the melanosomes, dopaquinone reacts in a eumelanogenesis or pheomelanogenesis process. If cysteine levels are low, dopaquinone is converted into eumelanin by autoxidation processes. If cysteine levels are high, dopaquinone combines with cysteine to form cysteinyldopa, which is subsequently modified to generate pheomelanin.

Melanin pigmentation of the skin can be divided into several causal components: 1) cutaneous melanin generated according to genetic programs in the absence of exposure to ultraviolet rays (constitutive skin color) and 2) immediate and delayed tanning reactions induced by direct exposure of the skin to UV radiation (facultative skin color). The changes in facultative color are a result of the interaction between sunlight, hormones and the tanning capacity, the latter being dependent on the genetic constitution of each individual.

All human beings, regardless of their skin and their hair color, have approximately the same amount of epidermal melanocytes in a given anatomical area. Ethnic color differences are due to differences in the properties of melanosomes and not to the amount of melanocytes. It must also be taken into consideration that the melanocyte distribution is not uniform in the skin and that there is approximately twice the number of melanocytes in the exposed areas than in the non-exposed areas.

Apparent changes in skin color occur throughout a person's lifetime and thus, for example, skin spots appear in the skin of the face, neck, neck-line and hands of older people which are clear signs of ageing [Piérard G. E., Piérard-Franchimont C., Laso Dosal F., Ben Mosbah T., Arrese Estrada J., Rurangirwa A., Dowlati A. and Vardar M. (1991) "Pigmentary changes in skin senescence" J. Appl. Cosmetol. 9:57-63]. This change in the number of age-dependent epidermal melanocytes has been quantified in a reduction of up to 10% in non-exposed areas of the skin per decade of life. The reduction in the number of melanocytes is lower in exposed areas due to the stimulating effect of UV radiation in the melanocyte population. Furthermore, continued overexposure to UV radiation causes accelerated ageing in the skin, known as photoageing, which is characterized by the onset at a much earlier age of the signs of skin ageing, including the onset of spots in those areas of the skin overexposed to UV radiation [Stefanaki C., Stratigos A. and Katsambas A. (2005) "Topical retinoids in the treatment of photoaging" J. Cosmet. Dermatol. 4:130-134].

It frequently occurs that the melanin density in the melanocytes is greater in an area of an individual's skin than in the surrounding areas and as a result the individual has a darker color in the affected area than in the rest. These areas are known as hyperpigmentation areas. Some of the causes of hyperpigmentation include hormonal alterations, melasma, lentigo, piebaldism, Addison's disease, hypersensitivity to ultraviolet radiation due to agents favoring the action of radiation (phototoxins), or hyperpigmentation resulting from an inflammatory lesion. Spots associated to acne, eczemas, scars or depilation belong to this latter type of hyperpigmentation and these spots can last even several years.

There are also areas of an individual's skin having lower melanin densities than in the surrounding areas. Said type of hypopigmented spots are known as vitiligo [Dooley T. P. (1994) "Recent advances in cutaneous melanoma oncogenesis research" Onco. Res. 6:1-9; Benmaman O. and Sanchez J. L. (1988) "Treatment and camouflaging of pigmentary disorders" Clin. Dermatol. 6:50-61; Schallreuter K. U. (1997) "Epidermal adrenergic signal transduction as part of the neuronal network in the human epidermis" J. Invest. Dermatol. 2:37-40]. Though it would be desirable to be able to restore pigmentation in the areas affected by vitiligo with topical application, it has been shown that this approach is extremely difficult in most subjects suffering vitiligo. An alternative to phototherapy with UVA rays or to the use of cosmetic make-up of the affected area with dihydroxyacetone lotions [Benmaman O. and Sanchez J. L. (1988) "Treatment and camouflaging of pigmentary disorders." Clin. Dermatol. 6:50-61] is the reduction of the degree of pigmentation of the non-affected surrounding skin to reduce the contrast between both areas.

Irregularities in pigmentation of the skin can also be caused by exposure to environmental factors. Exposure of the skin, especially Caucasian skin, to ultraviolet radiation, particularly UVB, promotes the synthesis of endogenous tyrosinase, resulting in an increase of melanogenesis and therefore in skin tanning. However, persistent exposure to UVB radiation can result in the formation of cancerous hyperpigmented lesions or melanomas [Dooley T. P. (1994) "Recent advances in cutaneous melanoma oncogenesis research" Onco. Res. 6:1-9] as well as in non-malignant hyperpigmented spots due to photoageing.

Furthermore, there is a market need consisting of depigmenting agents for lightening natural skin color due to the fact that a lighter skin color is perceived as more desirable for some dark-skinned people in different countries and races due to sociological or psychological reasons [Dooley T. P. (1997) "Is there room for a moderate level of regularity oversight?" in "Drug Discovery Approaches for Developing Cosmeceuticals: Advanced Skin Care and Cosmetic Products", Ed. Hori W, Chapter 1.4, International Business Communications, Southborough, Mass., USA; Dooley T. P. (1997) "Topical skin depigmentation agents: Current products and discovery of novel inhibitors of melanogenesis" J. Dermatol. Treat. 8:275-279].

In the same manner, within the beauty standards established in most countries and races, facial hair in women (known as hirsutism) is not desirable, especially dark facial hair, nor is body hair desirable. Despite the fact that different technologies such as depilation or laser treatment allow eliminating facial or body hair in a relatively effective manner, said treatments are usually painful or expensive, so there is a need for depigmenting agents which allow simply and effectively lightening the color of facial and body hair.

To modify the degree of pigmentation, it is even possible to inhibit melanin distribution in the epidermal cell layers or to cause melanin degradation by means of melanogenesis inhibitors which interact with enzyme tyrosinase or with any other enzyme involved in melanogenesis.

There is a strong demand for depigmenting agents which allow restoring spots or freckles to a normal skin color and therefore allow reducing the signs of ageing and of photoageing. For many years, skin depigmentation or lightening was done using very strong products such as hydroquinones or derivatives thereof, particularly their ethers such as monomethyl ether and monoethyl ether. Though these compounds show certain efficacy, they have adverse effects due to their toxicity, even making them hazardous. Thus, hydroquinone, for example, is irritating and cytotoxic for melanocytes, causes irreversible hypopigmentation, subsequently increasing photosensitization in areas of the skin exposed to UV radiation and has shown indications of mutagenicity [Glatt H., Padykula R., Berchtold G. A., Ludewig G., Platt K. L., Klein J. and Oesch F. (1989) "Multiple activation pathways of benzene leading to products with varying genotoxic characteristics" Environ Health Perspect 82:81-89; Glatt H. R. (1990) "Endogenous mutagens derived from amino acids." Mutat. Res. 238:235-243] and accordingly, its use is prohibited in some countries and legally limited in others to concentrations of less than 2%. Another widespread depigmenting agent is kojic acid and its family of derivatives. However, said compound is not problem-free since allergic reactions after continued use have been documented [Nakagawa M., Kawai K. and Kawai K. (1995) "Contact allergy to kojic acid in skin care products" Contact Dermatitis 42:9-13], and furthermore the compound is unstable in solution, making it difficult to manufacture compositions containing it.

Other rather aggressive chemical compounds that have been tested as depigmenting agents are peroxides, acids, mercury salts, formaldehyde or thiolated compounds. Many of these compounds have a rather pungent and/or unpleasant smell, rendering them unusable for marketing in cosmetic or pharmaceutical compositions.

Topical retinoids and corticosteroids have also been proposed as whitening agents, although they have failed to provide a favorable response. Arbutin and its derivatives are also used, though they are only marginal tyrosinase inhibitors and have little bioavailability. Other widely used depigmenting agents are vitamin C and its derivatives, such as ascorbyl-2-phosphate magnesium salt (MAP) or ascorbyl-2-phosphate sodium salt (NAP) for example, although they basically have the same instability drawbacks in formulations as those described for kojic acid.

Other recently proposed compositions use natural product extracts, some of which have been used as whitening agents for centuries in Asia or in Europe, such as lemon, orange, ginkgo, cucumber, geranium, bearberry, carob bean, cinnamon, marjoram, rosemary, clove, blackberry or licorice extracts. The variety of active ingredients in the extracts of these natural products and the possible allergic reactions of natural products occasionally limit the use of these natural agents.

The use of most whitening or depigmenting compounds whether for treating hyperpigmented areas or of areas next to hypopigmented areas, for aesthetic reasons to lighten the natural skin color, has a collateral effect of increasing the risk of damage due to UV radiation, since it decreases the amount of melanin produced by melanocytes. Melanin is the natural photoprotector of the skin, as it dissipates in the form of heat over 99.9% of absorbed UV radiation [Meredith P. and Riesz J. (2004) "Radiative Relaxation Quantum Yields for Synthetic Eumelanin" Photochem. Photobiol. 79:211-216]. This means that less than 0.1% of the absorbed radiation is able to generate free radicals, which are the agents causing direct and indirect damage to DNA and, therefore, of photoageing. The cosmetic and pharmaceutical sectors compensate for this deprotection inherent to the use of whitening or depigmenting agents by adding photoreactive substances or solar filters to their formulations. Solar filters protect the skin from UVB radiation, which can cause bums, and from UVA radiation, which causes long-term damage to the skin causing accelerated ageing or photoageing. Solar filters are classified into 1) chemical filters containing chemical compounds absorbing UV radiation and emitting it in the form of low-energy radiation that is not harmful for the skin, 2) physical filters containing opaque materials reflecting UV radiation or 3) biological filters preventing the formation of free radicals and enhance the cutaneous immunological system. However, many of these substances are potentially irritating, sensitizing or toxic, their use being regulated and even limited or prohibited in different countries. Therefore, there is a need to develop whitening or depigmenting compounds with intrinsic photoprotective efficacy which allows reducing the use of additional photoprotectors.

Thus there is a need to develop new, safer, more chemically stable molecules and/or molecules having greater efficacy than substances known in the state of the art for treating those conditions, disorders and/or pathologies of the skin, hair and/or nails in which a regulation or reduction of the amount of melanin produced by the melanocytes is desirable.

The applicant of the present invention has found that 6-substituted 7-methoxy-2,2-dimethylchromanes are capable of reducing the amount of melanin produced by the melanocytes by means of the inhibition of the enzyme tyrosinase and, in turn, to protect against damage caused by UV radiation.

In the state of the art, document EP 0655239 A1 discloses anticarcinogenic drugs containing 6,7-disubstituted 2,2-dialkylchromanes or 6,7-disubstituted 2,2-dialkylchromenes as anti-free radical agents.

Patent document JP 2001-002558 describes cosmetic compositions of 6,7-disubstituted 2,2-dialkylchromanes or 6,7-disubstituted 2,2-dialkylchromenes with hydroxy, methoxy or 2-trifluoroethoxy groups having a whitening effect and an effect of increasing the permeability of the epidermal barrier due to the fact that these compounds inhibit melanogenesis and sebaceous secretion in the skin.

Patent documents EP 1430879 A2, EP 1430933 A2 and EP 1336403 A1 describe the use of 6,7-disubstituted 2,2-dialkylchromanes or 6,7-disubstituted 2,2-dialkylchromenes with hydroxy, methoxy or 2-trifluoroethoxy groups in cosmetic deodorant or antiperspirant compositions, in compositions for treating hair loss and in compositions with anti-inflammatory activity, respectively.

Patent applications EP 1002533 A1 and EP 1430882 A2 describe cosmetic or dermatological compositions of 6,7-disubstituted 2,2-dimethylchromanes with hydroxy, methoxy or 2-trifluoroethoxy groups, alone or combined with other antioxidants, respectively. Patent documents EP 1634576 A1 and EP 1343465 A2 describe, among others, cosmetic compositions, 6-hydroxy-7-methoxy-2,2-dimethylchromane compositions (Lipochroman-6 marketed by Lipotec S.A.) or 6-hydroxy-7-methoxy-2,2-dimethylchromene combined with DNA-repair enzymes.

The use of Lipochroman-6 as an antioxidant agent inhibitor of lipid peroxidation in cosmetic or dermatological compositions is also known [Puig A. (2002) "Synthetic actives for cosmetic applications" Specialty Chemicals Magazine 2002, 22(10):16-17]. Lipochroman-6 also acts as an oxygen-reactive radical species scavenger [Sanvicens N., Gomez-Vicente V., Masip I., Messeguer A. and Cotter T. G. (2004) "Oxidative stress-induced apoptosis in retinal photoreceptor cells is mediated by calpains and caspases and blocked by the oxygen radical scavenger CR-6" J. Biol. Chem. 279(38):39268-39278] and inhibitor of tyrosine nitration by peroxynitrites [Cebrian J., Messeguer A., Facino R. M. and Garcia Anton J. M. (2005) "New anti-RNS and -RCS products for cosmetic treatment" Int. J. Cosm. Science 27(5):271-278], which are processes related to skin ageing.

Likewise, patent document EP 1267813 A2 describes Lipochroman-6 cosmetic compositions as an MMP-1 matrix metalloprotease inhibitor. Patent documents WO 01/82888 A1, WO 02/05778 A1 and WO 02/47655 A1 describe Lipochroman-6 compositions alone or combined with other compounds, wherein Lipochroman-6 is an NO-synthase inhibitor. Particularly patent document WO 01/82888 also describes the use of its compositions to inhibit melanogenesis induced by ultraviolet radiation and/or the treatment of hypermelanosis-type disorders.

None of the previously mentioned documents describes 6-substituted 7-methoxy-2,2-dimethylchromanes with an ester or thioester group with 3 to 24 carbon atoms ($C_3$-$C_{24}$), and which are chemically modified derivatives of 6-hydroxy-7-methoxy-2,2-dimethylchromane.

Only 6-heptyloxy-7-methoxy-2,2-dimethylchromene and 6-lauroyl-7-methoxy-2,2-dimethylchromene compounds obtained from 6-hydroxy-7-methoxy-2,2-dimethylchromene are known in the state of the art. However, the 6-heptyloxy-7-methoxy-2,2-dimethylchromane or 6-lauroyl-7-methoxy-2,2-dimethylchromane analogues are not known.

Therefore the synthesis of 6-substituted 7-methoxy-2,2-dimethylchromanes with an ester or thioester group with 3 to 24 carbon atoms ($C_3$-$C_{24}$) is an object of the present invention.

The applicant of the present invention has surprisingly found that these compounds also have greater depigmenting activity than the compounds known in the state of the art, and particularly greater than 6-substituted 7-methoxy-2,2-dimethylchromane compounds with hydroxy, methoxy or 2-trifluoroethoxy groups, with intrinsic photoprotective efficacy.

There is no indication in the state of the art of that esterification or thioesterification should increase the depigmenting efficacy, therefore a person skilled in the art could not deduce the nature of the modifications required in chromanes to enhance their whitening capacity.

Therefore, the present invention provides a novel solution to the existing needs and comprises the discovery of 6-substituted 7-methoxy-2,2-dimethylchromanes with an ester or thioester group with 3 to 24 carbon atoms ($C_3$-$C_{24}$) capable of treating those conditions, disorders and/or pathologies of the skin, hair and/or nails which require regulating the degree of pigmentation in a safer and more effective manner than the whitening compounds already known in the state of the art.

DESCRIPTION OF THE INVENTION

The present invention provides a simple, effective and risk-free solution for treating, caring for and/or cleaning skin, hair and/or nails, comprising applying on the skin, hair and/or nails of a mammal a 6-substituted 7-methoxy-2,2-dimethylchromane. The object of the present invention is also a cosmetic or pharmaceutical composition containing at least one 6-substituted 7-methoxy-2,2-dimethylchromane of formula (I) and a cosmetically or pharmaceutically acceptable medium.

In the description of the present invention, the terms "whitening" and "depigmenting" are used indistinctly throughout this document.

Therefore, a first aspect of the invention relates to a 6-substituted 7-methoxy-2,2-dimethylchromane compound according to general formula (I):

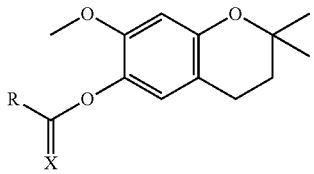

(I)

wherein X is selected from the group consisting of O or S; and

R is a linear or branched, saturated or unsaturated aliphatic group with from 2 to 23 carbon atoms ($C_2$ to $C_{23}$), or a cyclic group.

Preferred structures of the compounds depicted in general formula (I) are those in which R is a linear, saturated or unsaturated aliphatic group with from 2 to 23 carbon atoms ($C_2$ to $C_{23}$) or R is an alicyclic cyclic group, an aromatic cyclic group or a heterocyclic cyclic group.

Preferred structures of the compounds depicted in general formula (I) are those in which X is O.

Particularly preferred structures are those in which

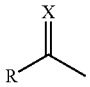

is an aliphatic group selected from the group consisting of tert-butanoyl, 2-methylhexanoyl, hexanoyl, octanoyl, decanoyl, lauroyl, myristoyl, palmitoyl, stearoyl, oleoyl or linoleoyl.

Additionally, preferred structures those are in which

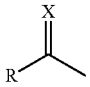

is an alicyclic, aromatic or heterocyclic cyclic group selected from the group consisting of —CO—$(CH_2)_{0-6}$-phenyl, —CO—$(CH_2)_{0-6}$-(1-naphthyl), —CO—$(CH_2)_{0-6}$-(2-naphthyl), —CO—$(CH_2)_{0-6}$-CH(phenyl)$_2$, —CO-(2-fluorophenyl), —CO-cyclohexyl, α-lipoyl, L-prolyl, D-prolyl, biotinyl —CO-(4-imidazolyl), —CO-(2-pyridyl), —CO-(2-thienyl), —CO-(2-furyl) or —CO-(3-furyl).

In the context of the present invention, the term "aliphatic group" relates to a linear or branched, saturated or unsaturated hydrocarbon group.

The term "hydrocarbon group" is used in the present invention to comprise, for example and in a non-limiting sense, alkyl, alkenyl and alkynyl groups.

The term "alkyl group" relates to a saturated, linear or branched hydrocarbon group, including, for example and in a non-limiting sense, methyl, ethyl, isopropyl, isobutyl, tertbutyl, heptyl, dodecyl, hexadecyl, octadecyl, amyl, 2-ethylhexyl, 2-methylhexyl, 2-methylbutyl, 5-methylhexyl and the like.

The term "alkenyl group" relates to an unsaturated, linear or branched hydrocarbon group with one or more carbon-carbon double bonds such as, for example and in a non-limiting sense, the vinyl, oleyl, linoleyl group and the like.

The term "alkynyl group" relates to an unsaturated, linear or branched hydrocarbon group with one or more carbon-carbon triple bonds.

The term "cyclic group" relates to a closed hydrocarbon ring which can be classified as an alicyclic, aromatic or heterocyclic group.

The term "alicyclic group" relates to a cyclic hydrocarbon group with properties similar to aliphatic groups, including, for example and in a non-limiting sense, cyclopropyl, cyclopentyl, cyclohexyl and the like.

The term "aromatic group" or the term "aryl group" relate to a mono- or polycyclic aromatic hydrocarbon group or to an aralkyl group.

The term "aralkyl group" relates to an alkyl group substituted with one or more aromatic groups, including, for example and in a non-limiting sense, —$(CH_2)_{1-6}$-phenyl, —$(CH_2)_{1-6}$-(1-naphthyl), —$(CH_2)_{1-6}$-(2-naphthyl), —$(CH_2)_{1-6}$-CH(phenyl)$_2$ and the like.

The term "heterocyclic group" relates to a closed hydrocarbon ring in which one or more than one of the atoms of the ring is an element other than carbon, such as nitrogen, oxygen or sulfur for example, or an heteroalkyl group.

The term "heteroalkyl group" relates to an alkyl group substituted with a heterocyclic group, including, for example and in a non-limiting sense, —$(CH_2)_{1-6}$-imidazolyl, —$(CH_2)_{1-6}$-thienyl, —$(CH_2)_{1-6}$-furyl, —$(CH_2)_{1-6}$-pyrrolidinyl and the like.

As is understood in this technical field, a high degree of substitution is not only tolerated but it is advised. Substitution can therefore exist in the compounds of the present invention. For the purpose of simplifying the present description of the invention, the terms "group" and "block" will be used to differentiate between chemical species which allow substitution or which can be substituted ("group"), and those which do not allow substitution or which cannot be substituted ("block"). For example, the expression "aliphatic group" will include not only aliphatic substituents, but also aliphatic substituents containing other substituents known in the state of the art, such as hydroxy, alkoxy, amino, carboxyl, halogen atoms, cyano, nitro, alkylsulfonyl, and others. Thus, "aliphatic group" includes ether, haloalkyl, alcohol, thiol, carboxyl, amine, hydroxyalkyl, sulfoalkyl and guanidine groups and others. In contrast, the expression "aliphatic block" is limited only to the inclusion of aliphatic substituents, such as propyl, isobutyl, octyl, decyl, lauryl, myristyl, palmityl, stearyl, oleyl, linoleyl and the like.

The cosmetically or pharmaceutically acceptable salts of the compounds provided by this invention are within the scope of the present invention. The term "cosmetically or pharmaceutically acceptable salts" include the salts normally used to form base addition salts, whether they are metallic, such as and in a non-limiting sense lithium, sodium, potassium, calcium, magnesium or aluminum among others for example, or organic, such as and in a non-limiting sense ethylamine, diethylamine, ethylenediamine, ethanolamine, diethanolamine, arginine, lysine, histidine or piperazine among others for example, or acid addition salts, whether they are organic, such as and in a non-limiting sense acetate, citrate, oleate, trifluoroacetate, oxalate or gluconate among others for example, or inorganic, such as and in a non-limiting sense chloride, sulfate, borate or carbonate among others for example. The nature of the salt is not critical provided that it is cosmetically or pharmaceutically acceptable. The cosmetically or pharmaceutically acceptable salts of the compounds of the invention can be obtained by conventional methods well-known in the state of the art [Berge S. M., Bighley L. D. and Monkhouse D. C. (1977) "Pharmaceutical Salts" J. Pharm. Sci. 66:1-19].

The compounds object of the present invention can be synthesized according to conventional methods known in the state of the art, such as for example by esterification or thioesterification reactions starting from 6-hydroxy-7-methoxy-2,2-dimethylchromane and the compound of general formula (II), which is the acid or thioacid of the corresponding aliphatic or cyclic group or a reactive derivative thereof.

(II)

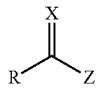

wherein X is selected from the group consisting of O or S;

R is a linear or branched, saturated or unsaturated aliphatic group with from 2 to 23 carbon atoms ($C_2$ to $C_{23}$), or a cyclic group; and Z is a free OH group, a reactive derivative thereof or a halogen.

For example, in one method of obtaining the compounds of general formula (I) a fragment of the compound of general formula (I) having a free hydroxyl group or a reactive derivative thereof is reacted with a complementary fragment of general formula (II) having a carboxyl or thiocarboxyl group or a reactive derivative thereof, with the subsequent formation of an ester or thioester bond, and in which said fragments have the functional groups that do not participate in the formation of the ester or thioester bond, if any, duly protected with temporary or permanent protecting groups. Examples of protecting groups, their insertion and their elimination, are described in the literature [Greene T. W. and Wuts P. G. M. (1981) in "Protective groups, in organic synthesis", John Wiley & Sons, New York, USA; Atherton E. and Sheppard R. C. (1984) in "Solid Phase Peptide Synthesis: A practical approach", IRL Press Oxford University, UK]. The term "protecting groups" also includes polymeric supports used in solid phase synthesis.

The compounds of the invention or their cosmetically or pharmaceutically acceptable salts can be administered for treating, caring for and/or cleaning skin, hair and/or nails by any means producing contact of the compounds with the action site thereof in the body of a mammal, preferably in a human being, in the form of a composition that contains them. In this sense, the invention provides cosmetic or pharmaceutical compositions comprising at least one compound of general formula (I) or its cosmetically or pharmaceutically acceptable salts together with at least one cosmetically or pharmaceutically acceptable adjuvant. Said compositions can be prepared by means of conventional methods known by persons skilled in the art [Wilkinson J. B. and Moore R. J. (1982) in "Harry's Cosmetology", Longman Scientific & Technical, London, UK; Faulí i Trill° C. (1993) "Tratado de Farmacia Galénica" Luzán 5, S.A. Eds, Madrid].

The compounds of the present invention can also be adsorbed on solid organic polymers or solid mineral supports such as, for example and in a non-limiting sense talc, bentonite, silica, starch and/or maltodextrin among others.

The cosmetic or pharmaceutical compositions containing the compounds of the present invention or their cosmetically or pharmaceutically acceptable salts can be used in different types of formulations for topical or transdermal application such as, for example and in a non-limiting sense, creams, oil and/or silicone in water emulsions, water in oil and/or silicone emulsions, water/oil or silicone/water type emulsions, oil or silicone/water/oil or silicone type emulsions, oils, milks, balsams, foams, lotions, hydroalcoholic solutions, gels, liniments, serums, soaps, ointments, mousses, salves, powders, bars, pencils or sprays or aerosols, including leave on and rinse-off formulations, and they can also be incorporated by means of techniques known by persons skilled in the art in different types of solid accessories such as, for example and in a non-limiting sense towelettes, hydrogels, adhesive (or non-adhesive) patches or face masks, or they can be incorporated in different makeup products such as, for example and in a non-limiting sense makeup bases, makeup removal lotions, makeup removal milks or under eye concealers, among others.

The cosmetic or pharmaceutical compositions containing the compounds of the present invention or their cosmetically or pharmaceutically acceptable salts can also be incorporated in products for treating, caring for and/or cleaning nails such as, for example and in a non-limiting sense polishes, nail polish removal lotions or cuticle removal lotions.

The pharmaceutical compositions containing the compounds of the invention or their cosmetically or pharmaceutically acceptable salts can be administered in addition to topically or transdermally, by any other type of suitable administration method, for example by oral, nasal, parenteral or rectal administration, to which end they will include the cosmetically or pharmaceutically acceptable excipients necessary for the formulation of the desired dosage form. In the context of the present invention, the term "parenteral" includes subcutaneous, intradermal, intravascular injections such as, for example and in a non-limiting sense intravenous, intramuscular, spinal, intracranial, intraarticular, intratecal and intraperitoneal, as well as any other similar injection or infusion technique. A review of the different pharmaceutical dosage forms and of the excipients necessary for obtaining them can be found, for example, in "Tratado de Farmacia Galénica", C. Faulí i Trillo, 1993, Luzán 5, S.A. Ediciones, Madrid.

Also, the cosmetic compositions containing the compounds of the present invention or their cosmetically or pharmaceutically acceptable salts can be used in different types of formulations for their oral administration, particularly in the form of oral cosmetics such as, for example and in a non-limiting sense, in capsules, including gelatin capsules, tablets, including sugar-coated tablets, powders, granulated forms, chewing gums, solutions, suspensions, emulsions, syrups, jellies or gelatins, as well as in any other presentation known by a person skilled in the art. Particularly, the compounds of the invention can be incorporated in any form of functional food or enriched food such as, for example and in a non-limiting sense, in dietary bars or in compact or non-compact powders. Said powders can be solubilized in water, soda, dairy products, soy derivatives or they can be incorporated in dietary bars. The compounds of the present invention or their cosmetically or pharmaceutically acceptable salts can be formulated with the usual excipients and adjuvants for oral compositions or food supplements such as, for example and in a non-limiting sense, fatty components, aqueous components, wetting agents, preservatives, texturizing agents, flavors, aromas, antioxidants and/or colorants common in the food sector.

The compounds of the invention or their cosmetically or pharmaceutically acceptable salts can also previously be incorporated in cosmetic or pharmaceutical sustained release systems and/or carriers such as liposomes, millipartícles, microparticles and nanoparticles, as well as in sponges, vesicles, micelles, millispheres, microspheres and nanospheres, lipospheres, millicapsules, microcapsules and nanocapsules, as well as in microemulsions and nanoemulsions, for the purpose of obtaining greater penetration of the active ingredient and/or improving the pharmacokinetic and pharmacodynamic properties thereof. The controlled release formulations can be prepared by means of methods known in the state of the art and can be administered, for example, by topical administration, including adhesive patches, or by oral, parenteral, rectal administration or subcutaneous implantation or by direct implantation in a specific part of the body, and they must preferably release a relatively constant amount of the compounds of the invention. The amount of compound contained in the controlled release formulation will depend on, for example, the administration site, the kinetics and the duration of the release of the compound of the invention.

The compounds of general formula (I) or their cosmetically or pharmaceutically acceptable salts are used in the cosmetic or pharmaceutical compositions of the present invention at cosmetically or pharmaceutically effective concentrations to obtain the desired effect; preferably between 0.00000001% (by weight) and 20% (by weight); preferably between 0.00001% (by weight) and 10% (by weight) and more preferably between 0.0001% (by weight) and 5% (by weight).

The cosmetically or pharmaceutically effective amount of the compounds according to the invention or of their cosmetically or pharmaceutically acceptable salts which must be administered to regulate the amount of melanin, as well as their dosage, will depend on a number of factors, including age, degree of pigmentation, administration method and frequency and particularly on the nature of the compounds that are used.

The cosmetically or pharmaceutically acceptable adjuvants contained in the cosmetic or pharmaceutical compositions described in the present invention include the additional ingredients commonly used in compositions for treating, caring for and/or cleaning skin, hair and/or nails such as, for example and in a non-limiting sense, other agents inhibiting melanin synthesis, other whitening or depigmenting agents, anti-ageing agents, agents inhibiting NO-synthase, antioxidants, anti-atmospheric pollution and/or free radical trapping agents, anti-glycation agents, emulsifying agents, emollients, organic solvents, liquid propellants, skin conditioners such as for example wetting agents, moisture retaining substances, alpha hydroxy acids, moisturizers, vitamins, pigments or colorants, dyes, gelling polymers, thickeners, surfactants, softeners, anti-wrinkle agents, agents capable of reducing or eliminating bags under the eyes, exfoliating agents, antimicrobial agents, antifungal agents, bactericides, agents stimulating dermal or epidermal macromolecule synthesis and/or capable of preventing or inhibiting their degradation, such as for example agents stimulating collagen synthesis, agents stimulating elastin synthesis, agents stimulating decorin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating lipid synthesis and synthesis of components of the stratum corneum (ceramides, fatty acids, etc.), dermorelaxing agents, agents stimulating glycosaminoglycan synthesis, DNA repair agents, DNA protecting agents, agents stimulating defensin synthesis, agents stimulating chaperone synthesis, anti-pruritus agents, agents for treating sensitive skin, reaffirming agents, anti-stretch mark agents, astringent agents, sebum production regulating agents, agents stimulating lipolysis, anti-cellulite agents, calming agents, anti-inflammatory agents, agents acting on capillary circulation and/or microcirculation, agents acting on cell metabolism, agents intended to improve the dermalepidermal junction, preservatives, perfumes, chelating agents, plant extracts, essential oils, marine extracts, agents derived from a biofermentation process, mineral salts, cell extracts and/or solar filters (organic or mineral photoprotective agents active against ultraviolet A and B rays) among others, provided that they are physically and chemically compatible with the remaining components of the composition and especially with the compounds of general formula (I) contained in the composition of the present invention. Likewise, the nature of said additional ingredients must not unacceptably alter the benefits of the compounds of the present invention. Said additional ingredients may be of a synthetic or natural origin, such as for example plant extracts, or they can be derived from a biofermentation process. Additional examples are described in CTFA Cosmetic Ingredient Handbook, Eleventh Edition (2006).

The compounds of the present invention can be used in combination with solar filters (UVA or UVB radiation blockers) to prevent repigmentation, to protect the skin from exposure to the sun or from tanning induced by exposure to the sun, or to increase their capacity to reduce the amount of melanin in the skin and its depigmenting action. Examples of solar filters include, for example and in a non-limiting sense, p-aminobenzoic acid derivatives, benzylidene camphor derivatives, cinnamic acid derivatives, benzothiazole derivatives, benzimidazole derivatives, benzophenone derivatives, triazine derivatives, salicylic acid derivatives, dibenzoylmethane derivatives, β,β-diphenylacrylate derivatives, as well as nanopigments such as, for example and in a non-limiting sense, titanium oxide nanopigments, iron oxide nanopigments, zinc oxide nanopigments, zirconium oxide nanopigments or cerium oxide nanopigments, among others.

Likewise, the compounds of the present invention can also be used in combination with desquamating agents capable of promoting exfoliation of the skin for the purpose of obtaining greater efficacy in the depigmenting treatment. Examples of desquamating agents include the use of alpha hydroxy acids such as, for example and in a non-limiting sense, glycolic acid, lactic acid, citric acid, tartaric acid, malic acid and/or mandelic acid among others, beta hydroxy acids such as, for example and in a non-limiting sense salicylic acid and derivatives thereof; as well as the use of urea and derivatives thereof, resveratrol, N-acetylglucosamine, jasmonic acid and derivatives thereof, cinnamic acid, gentisic acid, oligofucoses, Saphora japonica extract, detergents and/or enzymes such as, for example and in a non-limiting sense, sutilains, papaya extract, bromelain, pineapple extract, pumpkin extract and/or sweet potato extract, among others.

The compounds object of the present invention have variable solubility in water, depending on the nature of the R and X groups in general formula (I). Those compounds that are not soluble in water can be solubilized in cosmetically or pharmaceutically acceptable conventional solvents such as, for example and in a non-limiting sense, ethanol, propanol or isopropanol, propyleneglycol, glycerin, butylene glycol or polyethylene glycol, or in any combination thereof or combination thereof with water.

The cosmetic or pharmaceutical compositions containing the compounds of the invention or their cosmetically or pharmaceutically acceptable salts can be administered orally or topically or transdermally and they can be presented in any dosage form, for example, solid, liquid or semisolid, to which end they will include the pharmaceutically acceptable excipients necessary for the formulation of the desired dosage form [Faulí i Trill° C. (1993) in "Tratado de Farmacia Galénica", Luzán 5, S.A. Ediciones, Madrid]. The cosmetic or pharmaceutical compositions of the invention can include agents which increase percutaneous absorption of the compounds of the present invention such as, for example and in a non-limiting sense, dimethylsulfoxide, dimethylacetamide, dimethylformamide, surfactants, azone, alcohol, acetone, propyleneglycol or polyethylene glycol, among others. Likewise, the cosmetic or pharmaceutical compositions object of the present invention can be applied in the local areas to be treated by means of iontophoresis, sonophoresis, electroporation, steam wrap, microinjections or needleless injections by means of pressure such as, for example and in a non-limiting sense, oxygen pressure injections, for the purpose of obtaining greater penetration of the active ingredient.

The compounds of the invention or their cosmetically or pharmaceutically acceptable salts can also be incorporated into fabrics for making garments that are in direct contact with the skin of the body, such that they release the compounds of the invention either by biodegradation of the system for anchoring them to the fabric or by the friction of the garments against the body, due to body moisture, the pH of the skin or the body temperature. Examples of garments, fabrics and means for immobilizing the compounds in the fabrics, including microencapsulation, are described in the literature and are known in the state of the art [Schaab C. K. (1986) "Impregnating Fabrics With Microcapsules" HAPPI May 1986; Nelson G. (2002) "Application of microencapsulation in textiles" Int. J. Pharm. 242:55-62]. The preferred garments of the present invention are bandages, gauzes, pantyhose, socks, gloves or sleeves for the arms and forearms.

An additional aspect of the present invention relates to a cosmetic or pharmaceutical composition containing a cosmetically or pharmaceutically effective amount of at least one compound of the invention or its cosmetically or pharmaceutically acceptable salts, and furthermore a cosmetically or pharmaceutically effective amount of at least one extract with depigmenting activity such as, for example and in a non-limiting sense, Achillea millefolium, Aloe vera, Azadirachta indica, Osmunda japonica, Artocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifraga sarmentosa, Scutellaria galericulata, Sedum sarmentosum Bunge, Stellaria medica, Triticum Vulgare, Uva ursi or Withania somnifera extracts, among others, and/or furthermore a cosmetically or pharmaceutically effective amount of at least one synthetic compound, extract or product derived from a biofermentation process with depigmenting activity such as, for example and in a non-limiting sense, Lipochroman-6 [INCI: Dimethylmethoxy Chromanol] (6-hydroxy-7-methoxy-2,2-dimethylchromane) marketed by Lipotec, Actiwhite™ LS9808 [INCI: Aqua, Glycerin, Sucrose Dilaurate, Polysorbate 20, Pisum sativum (Pea) extract] or Dermawhite® NF L59410 [INCI: Mannitol, Arginine HCl, Phenylalanine, Disodium EDTA, Sodium Citrate, Kojic Acid, Citric Acid, Yeast Extract] marketed by Laboratoires Serobiologiques, Lumiskin™ [INCI: Caprylic/Capric Triglyceride, Diacetyl-Boldine], Melaclear™ [INCI: Glycerin, Aqua, Dithiaoctanediol, Gluconic acid, Sutilains, Beta-carotene] or Etioline™ [INCI: Glycerin, Butylene Glycol, Arctostaphylos uva ursi Leaf Extract, Mitracarpus scaber Extract] marketed by Sederma, Sepiwhite™ MSH [INCI: Undecylenoyl Phenylalanine] marketed by Seppic, Achromaxyl [INCI: Aqua, Brassica napes extract] marketed by Vincience, Gigawhite™ [INCI: Aqua, Glycerin, Melva sylvestris (Mallow) Extract, Mentha piperita Leaf Extract, Primula veris Extract, Alchemilla vulgaris Extract, Veronica officinalis Extract, Melissa officinalis Leaf Extract, Achillea millefolium Extract], Melawhite® [INCI: Leukocyte Extract, AHA] (leukocyte extract, alpha hydroxy acids) or Melfade®-J [INCI: Aqua, Arctostaphylos uva-ursi Leaf Extract, Glycerin, Magnesium Ascorbyl Phosphate] marketed by Pentapharm, Albatin® [INCI: Amino ethyl phosphoric Acid, Butylene Glycol, Aqua] marketed by Exsymol, Tyrostat™-11 [INCI: Aqua, Glycerin, Rumex occidentalis Extract] or Melanostatine®-5 [INCI: Dextran, Nonapeptide-1] marketed by Atrium, arbutin and its isomers, kojic acid and derivatives thereof, vitamin C and derivatives thereof such as, for example and in a non-limiting sense, 6-O-palmitoylascorbic acid, dipalmitoylascorbic acid, magnesium salt of ascorbic acid-2-phosphate (MAP), sodium salt of ascorbic-acid-2-phosphate (NAP), ascorbyl glucoside or ascorbyl tetraisopalmitate (VCIP) among others, retinol and derivatives thereof including tretinoin and isotretinoin, idebenone, hydroxybenzoic acid and derivatives thereof, flavonoids, soy extract, lemon extract, orange extract, ginkgo extract, cucumber extract, geranium extract, bearberry extract, carob bean extract, cinnamon extract, marjoram extract, rosemary extract, clove extract, soluble licorice extract, blackberry leaf extract, niacinamide, liquiritin, resorcinol and derivatives thereof, hydroquinone, α-tocopherol, γ-tocopherol, azelaic acid, resveratrol, mercury salts, linoleic acid, α-lipoic acid, dihydrolipoic acid, alpha hydroxy acids, beta hydroxy acids, ellagic acid, ferulic acid, cinnamic acid, oleanolic acid, aloesin and derivatives thereof and/or serine protease inhibitors such as, for example and in a non-limiting sense, tryptase, trypsin or PAR-2 inhibitors, among others.

Another aspect of the present invention relates to a cosuretic or pharmaceutical method to treat those conditions of mammals, preferably humans, requiring pigmentation regulation, comprising the administration of an effective amount of at least one compound of general formula (I) or its cosmetically or pharmaceutically acceptable salts, preferably in the form of a cosmetic or pharmaceutical composition which contains them. The present invention further provides a cosmetic or pharmaceutical method to whiten or lighten the skin, preferably the skin of the face and/or the hands. Likewise, the present invention provides a cosmetic or pharmaceutical method to treat those conditions, disorders and/or pathologies of the skin relating to regulation of pigmentation, preferably freckles, lentigo, melasma, piebaldism, Addison's disease, vitiligo, spots due to exposure to UV radiation, spots due to ageing or to photoageing, spots of an inflammatory origin and especially post-laser treatment or post-aesthetic surgery inflammations, spots due to acne, to eczemas, to ochronosis, to scars and/or to hormonal disorders such as chloasmas for example, which comprises applying on the skin a cosmetic or pharmaceutical composition containing at least one compound of the invention or its cosmetically or pharmaceutically acceptable salts. The present invention further provides a cosmetic or pharmaceutical method to depigment facial and/or body hair as well as to lighten the color of the hair which comprises applying on the scalp or on those areas of the human body with hair, a cosmetic or pharmaceutical composition containing at least one compound of the invention or its cosmetically or pharmaceutically acceptable salts. Likewise, the present invention provides a cosmetic or pharmaceutical method to qualify skin pigmentation irregularities, preferably the areas of the skin adjacent to the areas affected by vitiligo, reducing the contrast between both areas, which comprises applying on the skin a cosmetic or pharmaceutical composition containing at least one compound of the invention or its cosmetically or pharmaceutically acceptable salts. The present invention further provides a cosmetic or pharmaceutical method to photoprotect skin, hair and nails which comprises applying on the skin, hair and/or nails a cosmetic or pharmaceutical composition containing at least one compound of the invention or its cosmetically or pharmaceutically acceptable salts. The present invention further provides a cosmetic or pharmaceutical method to treat spots on nails which comprises applying on the nails a cosmetic or pharmaceutical composition containing at least one compound of the invention or its cosmetically or pharmaceutically acceptable salts.

The application frequency of the cosmetic or pharmaceutical composition comprising at least one compound of the invention or its cosmetically or pharmaceutically acceptable salts may significantly vary, depending on the needs of each subject, an application range from once a month up to 10 times a day being suggested, preferably from once a week up to 4 times a day, more preferably from three times a week up to three times a day, even more preferably one or two times a day.

An additional aspect of the present invention relates to the use of at least one of the compounds of general formula (I) or its cosmetically or pharmaceutically acceptable salts in preparing a cosmetic or pharmaceutical composition for treating, caring for and/or cleaning skin, hair and/or nails preferably the skin of the face, neck, neck-line, hands, axillae, groin, elbows and/or knees and more preferably local areas of the face, neck and/or hands.

According to an important aspect, the present invention relates to the use of at least one of the compounds of general formula (I) or its cosmetically or pharmaceutically acceptable salts in preparing a cosmetic or pharmaceutical composition for lightening or evening out pigmentation of the skin.

According to another important aspect, the present invention relates to the use of at least one of the compounds of general formula (I) or its cosmetically or pharmaceutically acceptable salts in preparing a cosmetic or pharmaceutical composition for treating spots on the skin.

According to another important aspect, the present invention relates to the use of at least one of the compounds of general formula (I) or its cosmetically or pharmaceutically acceptable salts in preparing a cosmetic or pharmaceutical composition for treating or preventing ageing or photoageing of the skin.

Another additional aspect of the present invention relates to the use of at least one of the compounds of general formula (I) or its cosmetically or pharmaceutically acceptable salts in preparing a cosmetic or pharmaceutical composition for photoprotecting the skin, hair and/or nails.

Another additional aspect of the present invention relates to the use of at least one of the compounds of general formula (I) or its cosmetically or pharmaceutically acceptable salts in preparing a cosmetic or pharmaceutical composition for lightening or depigmenting facial and/or body hair.

Another additional aspect of the present invention relates to the use of at least one of the compounds of general formula (I) or its cosmetically or pharmaceutically acceptable salts in preparing a cosmetic or pharmaceutical composition for treating spots on nails.

Additionally, the present invention provides a cosmetic or pharmaceutical depigmenting or whitening method, comprising the administration of an effective amount of at least one of the compounds of general formula (I) or its cosmetically or pharmaceutically acceptable salts, and preferably in the form of a cosmetic or pharmaceutical composition which contains it.

EXAMPLES

The following specific examples provided herein serve to illustrate the nature of the present invention. These examples are included only for illustrative purposes and must not be interpreted as being limitations to the invention herein claimed.

General Methodology

All the reagents and solvents are of synthesis quality and are used with no additional treatment.

Abbreviations:

DNA, deoxyribonucleic acid; QSF, quantity sufficient for; DCC, N,N-dicyclohexylcarbodiimide; DMAP, dimethylaminopyridine; DMSO, dimethylsulfoxide; DMEM, Dulbecco's modified Eagle's medium; DPPC, dipalmitoylphosphatidylcholine; equiv., equivalents; ESI-MS, electrospray ionization mass spectrometry; FBS, fetal bovine serum; HEPES, N-2-hydroxyethylpiperazine-N'-2-ethanesulfonic acid; HPLC, high performance liquid chromatography; MAP, ascorbyl-2-phosphate magnesium salt; MLU, multilaminar vesicles; MW, molecular weight; PMA, 1-methoxy-2-propyl acetate; ULV, unilaminar vesicles; UV ultraviolet; UVA, ultraviolet radiation type A; UVB, ultraviolet radiation type B.

Example 1 (*Partly Prophetic*)

Preparation of 6-substituted 7-methoxy-2,2-dimethylchromanes 6-hydroxy-7-methoxy-2,2-dimethylchromane (5.0 g; 24.0 mmol, 1 equiv.) was reacted with 1 equiv. of the corresponding carboxylic or thiocarboxylic acid in the presence of DMAP (2.0 mmol, 0.083 equiv.) and DCC (24.0 mmol, 1 equiv.) in dichloromethane at room temperature, performing controls by thin layer chromatography. When it was observed that the reaction stopped progressing the formed dicyclohexylurea was filtered and evaporated to dryness. The obtained compounds were purified by silica column chromatography by eluting with n-hexane and ethyl acetate and were characterized by ESI-MS. *In the table below, examples where no experimental molecular weight is given are prophetic examples.*

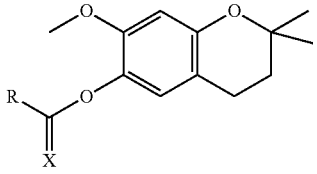

| | Theo-retical MW | Experi-mental MW |
|---|---|---|
| X = O<br>R = $CH_3CH_2$— | 264.32 | [264.39] |
| X = O<br>R = $CH_3(CH_2)_4$ | 306.40 | [306.35] |
| X = O<br>R = $CH_3(CH_2)_6$ | 334.45 | [334.40] |
| X = O<br>R = $CH_3(CH_2)_7$ | 348.48 | [348.54] |
| X = O<br>R = $CH_3(CH_2)_8$ | 362.50 | [362.48] |
| X = O<br>R = $CH_3(CH_2)_9$ | 376.53 | [376.57] |
| X = O<br>R = $CH_3(CH_2)_{10}$ | 390.56 | [390.51] |
| X = O<br>R = $CH_3(CH_2)_{12}$ | 418.61 | [418.53] |
| X = O<br>R = $CH_3(CH_2)_{14}$ | 446.66 | 446.62 |
| X = O<br>R = $CH_3(CH_2)_{16}$ | 474.72 | [474.79] |
| X = O<br>R = $CH_3(CH_2)_{18}$ | 502.77 | [502.83] |
| X = O<br>R = $CH_3(CH_2)_{20}$ | 530.82 | [530.88] |
| X = O<br>R = $CH_3(CH_2)_{22}$ | 558.88 | [558.85] |
| X = O<br>R = $CH_3(CH_2)_4(CH{=}CHCH_2)_4CH_2CH_2$ | 454.64 | [454.59] |
| X<br>R = cis $CH_3(CH_2)_5CH{=}CH(CH_2)_7$ | 444.65 | [444.63] |
| X<br>R = cis $CH_3(CH_2)_{10}CH{=}CH(CH_2)_4$ | 472.70 | [472.67] |
| X = O<br>R = cis $CH_3(CH_2)_7CH{=}CH(CH_2)_{13}$ | 556.86 | [556.92] |
| X = O<br>R = CH3CH2CH=CHCH$_2$CH=CHCH$_2$CH=CH$(CH_2)_7$ | 468.67 | [468.71] |
| X = O<br>R = $CH_3CH(CH_3)(CH_2)_{14}$ | 474.72 | [474.77] |
| X = O<br>R = $CH_3(CH_2)_4CH{=}CHCH_2CH{=}CH(CH_2)_7$ | 470.68 | [470.63] |
| X = O<br>R = trans $CH_3(CH_2)_7CH{=}CH(CH_2)_7$ | 472.70 | [472.76] |
| X = O<br>R = cis $CH_3(CH_2)_7CH{=}CH(CH_2)_7$ | 472.70 | [472.67] |
| X = O<br>R = cis $CH_3(CH_2)_7CH{=}CH(CH_2)_{11}$ | 528.81 | [528.89] |
| X = O<br>R = $CH_3(CH_2)_5CH(OH)CH_2CH{=}CH(CH_2)_7$ | 488.70 | [488.75] |
| X = O<br>R = $CH_2{=}CH(CH_2)_8$ | 374.51 | [374.56] |
| X = O<br>R = $(CH_3)_3$—C | 292.37 | [292.28] |
| X = O<br>R = $CH_3$—$(CH_2)_3$—$CH(CH_3)$ | 320.42 | [320.41] |
| X = O<br>R = cyclohexyl | 318.41 | [318.22] |
| X = O<br>R = $C_6H_5$ | 312.36 | [312.44] |
| X = O<br>R = 2 fluorophenyl | 330.35 | [330.42] |
| X = O<br>R = $C_6H_5$—$CH_2$ | 326.39 | [326.33] |
| X = O<br>R = 1-naphthyl | 362.42 | [362.18] |
| X = O<br>R = 2-naphthyl | 362.42 | [362.44] |
| X = O | 396.57 | 396.63 |

-continued

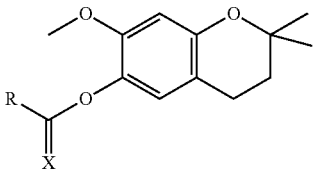

| | Theo-retical MW | Experi-mental MW |
|---|---|---|
| R = 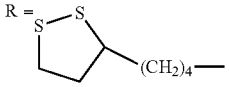 | | |
| X = O | 434.55 | [434.52] |
| *R* = 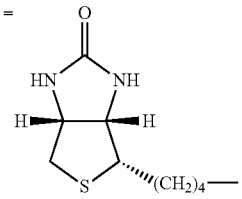 | | |
| X = O<br>R = 4-imidazolyl | 302.33 | [302.39] |
| X = O<br>R = 2-pyridyl | 313.35 | [313.43] |
| X = O<br>R = 2-thienyl | 318.39 | [318.41] |
| X = O<br>R = 2-furyl | 302.32 | [302.27] |
| X = O<br>R = 3-furyl | 302.32 | [302.35] |
| X = O<br>R = (R)-2-pyrrolidinyl | 305.37 | [305.42] |
| X = O<br>R = (S)-2-pyrrolidinyl | 305.37 | [305.39] |
| X = S<br>R = $C_6H_5$—$CH_2$ | 342.45 | [342.47] |
| X = S<br>R = tert butyl | 308.44 | [308.51] |
| X = S<br>R = (4-tert-butyl)phenyl | 384.53 | [384.52] |
| X = S<br>R = (2-hydroxy)phenyl | 344.43 | [344.47] |

Example 2 (*Prophetic*)

Preparation of a Cosmetic Composition Containing 7-methoxy-6-palmitoyl-2,2-dimethylchromane The following formulation [was] *is* prepared as described in the present invention:

The components of Phase A [were] *are* weighed in a large enough reactor and the mixture is heated to 70° C. to melt the waxes. The components of Phase B are weighed in a suitable container for the entire content. The components of Phase C are added to Phase B and heated to 70° C. under intense stirring. Then Phase A is slowly added to the preceding mixture under stirring and the mixture is maintained under stirring for 30 minutes at 70° C. It is left to cool under gentle stirring and when the mixture is at room temperature, xanthan gum and fragrance are added, the mixture is homogenized and the pH is corrected with triethanolamine if needed.

The cream that is obtained has a pH between 5.5 and 6.

| INGREDIENT (INCI Nomenclature) | % BY WEIGHT |
|---|---|
| PHASE A | |
| MINERAL OIL | 3.00 |
| 7-methoxy-6-palmitoyl-2,2-dimethylchromane | 0.10 |
| POLYACRYLAMIDE, C13-14 ISOPARAFFIN, LAURETH-7 | 2.00 |
| ETHYLHEXYL SALICILATE | 1.00 |
| BUTYL METHOXYD1BENZOYLMETHANE | 1.00 |
| ETHYLHEXYL METHOXYCINNAMATE | 7.50 |
| DIMETHICONE | 1.00 |
| CETEARYL ALCOHOL | 2.00 |
| SODIUM STEAROYL LACTYLATE | 1.50 |
| POLYGLYCERYL-3 STEARATE | 1.50 |
| 1 METHYLENE BIS-BENZOTRIAZOLYL TETRAMETHYLBUTYLPHENOL, AQUA (WATER), DECYL GLUCOSIDE, PROPYLENE GLYCOL, XANTHAN GUM | 3.00 |
| SQUALANE | 3.00 |
| GLYCERYL STEARATE | 2.00 |
| PHASE B | |
| DISODIUM EDTA | 0.30 |
| AQUA (WATER) | 55.82 |
| PHENOXYETHANOL, METHYLPARABEN, ETHYLPARABEN, BUTYLPARABEN, PROPYLPARABEN, ISOBUTYLPARABEN | 0.47 |
| IMIDAZOLIDINYL UREA | 0.10 |
| PHASE C | |
| TITANIUM DIOXIDE | 2.00 |
| GLYCERINE | 4.00 |
| PHASE D | |
| XANTHAN GUM | 0.35 |
| PHASE E | |
| PARFUME (FRAGRANCE) | 0.20 |
| PHASE F | |
| TRIETHANOLAMINE | QSF |

Example 3 (*Prophetic*)

Preparation of Liposomes Containing 7-methoxy-6-palmitoyl-2,2-dimethylchromane

Dipalmitoylphosphatidylcholine (DPPC), cholesterol and 7-methoxy-6-palmitoyl-2,2-dimethylchromane are weighed and dissolved in chloroform. The solvent is evaporated under vacuum until obtaining a thin phospholipid layer, and this is hydrated by treating at 55° C. with an aqueous solution containing Phenonip®, obtaining the MLV liposomes. The ULV liposomes are obtained by submerging the MLV liposomes in an ultrasound bath at 55° C. for 8 2-minute cycles at 5 minute intervals. To reduce the size even more, it can be passed through an extrusion system under high pressure.

| INGREDIENT (INCI Nomenclature) | % BY WEIGHT |
|---|---|
| DIPALMITOYLPHOSPHATIDYLCHOLINE | 8.0 |
| 7-methoxy-6-palmitoyl-2,2-dimethylchromane | 1.0 |
| CHOLESTEROL | 3.0 |
| PHENOXYETHANOL, METHYLPARABEN, ETHYLPARABEN, BUTYLPARABEN, PROPYLPARABEN, ISOBUTYLPARABEN | 0.5 |
| AQUA (WATER) | 87.5 |

Example 4 (*Prophetic*)

Preparation of a Composition in the Form of a Liposome Gel Containing 7-methoxy-6-palmitoyl-2,2-dimethylchromane The liposomes of example 3 are dispersed in water with preservatives (EDTA, imidazolidinyl urea and Phenonip®) under gentle stirring. Hispagel® 200 [INCI Aqua, Glycerin and Glyceryl polyacrylate] is added and it is gently stirred until a homogenous mixture is obtained.

| INGREDIENT (INCI Nomenclature) | % BY WEIGHT |
|---|---|
| LIPOSOMES CONTAINING 7-methoxy-6-palmitoyl-2,2-dimethylchromane (1%) | 10.00 |
| DISODIUM EDTA | 0.15 |
| IMIDAZOLIDINYL UREA | 0.10 |
| AQUA (WATER), GLYCERIN, GLYCERYL POLYACRYLATE | 60.00 |
| AQUA (WATER) | 29.25 |
| PHENOXYETHANOL, METHYLPARABEN, ETHYLPARABEN, BUTYLPARABEN, PROPYLPARABEN, ISOBUTYLPARABEN | 0.50 |

Example 5 (*Prophetic*)

Preparation of a Nail Polish Composition Containing 7-methoxy-6-palmitoyl-2,2-dimethylchromane 7-methoxy-6-palmitoyl-2,2-dimethylchromane is weighed with the acrylate copolymer and they are dissolved in ethanol by stirring vigorously. Acetone is added and it is conserved in a covered container to minimize evaporation.

| INGREDIENT (INCI Nomenclature) | % BY WEIGHT |
|---|---|
| ACRYLATES COPOLYMER | 22.0 |
| ETHYL ALCOHOL | 65.4 |
| ACETONE | 12.5 |
| 7-methoxy-6-palmitoyl-2,2-dimethylchromane | 0.1 |

Example 6 (*Prophetic*)

Preparation of a Composition to Depigment Body Hair Containing 7-methoxy-6-palmitoyl-2,2-dimethylchromane Heat Phase A and Phase B separately at 70-75° C. Add A to B under intense stirring. Allow it to cool, maintaining stirring at room temperature, add Phase C and neutralize with triethanolamine until obtaining pH 6.5.

| INGREDIENT (INCI Nomenclature) | % BY WEIGHT |
|---|---|
| PHASE A | |
| MINERAL OIL | 10.00 |
| PETROLATUM | 1.00 |
| BEESWAX (CERA ALBA) | 2.00 |
| 7-methoxy-6-palmitoyl-2,2-dimethylchromane | 0.50 |
| CETEARETH-25 | 2.00 |
| DIMETHICONE | 0.20 |
| C24-28 ALKYL METHICONE | 0.10 |
| CETEARYL ALCOHOL | 2.00 |

-continued

| INGREDIENT (INCI Nomenclature) | % BY WEIGHT |
|---|---|
| PHASE B | |
| DISODIUM EDTA | 0.15 |
| AQUA (WATER) | QSF 100 |
| PHENOXYETHANOL, METHYLPARABEN, ETHYLPARABEN, BUTYLPARABEN, PROPYLPARABEN, ISOBUTYLPARABEN | 0.50 |
| IMDDAZOLEDINYL UREA | 0.10 |
| CARBOMER | 0.35 |
| GLYCERINE | 3.00 |
| PHASE C | |
| PARFUME (FRAGRANCE) | 0.10 |
| PHASE F | |
| TRIETHANOLAMINE | QSF |

Example 7

Comparative Activity Assay of 7-methoxy-6-palmitoyl-2,2-dimethylchromane on the Action of Mushroom Tyrosinase In Vitro The assay is performed in 96 well plates and the samples are performed in triplicate. The control sample contains 80 μL of buffer (150 mM HEPES), 10 μL of mushroom tyrosinase of 10 μg/μL and 10 μL of 10 mM L-Dopa substrate. The positive control further contains kojic acid at a concentration of 0.1 mM. The samples of 7-methoxy-6-palmitoyl-2,2-dimethylchromane and 6-hydroxy-7-methoxy-2,2-dimethylchromane (Lipochroman-6) contain instead of kojic acid, the compounds at a concentration of 1 mM. The samples thus prepared are incubated at 37° C. for 10 minutes. Then the plate containing the samples is cooled for 5 minutes on ice to stop the enzymatic reaction. To quantify the melanin produced it is measured in the plate reader at a length of 492 nm.

Table 1 measures the percentage of melanin formed normalized in relation to the control sample for the comparative sample with kojic acid and for the sample with 7-methoxy-6-palmitoyl-2,2-dimethylchromane and for the Lipochroman-6 sample.

TABLE 1

| COMPOUND | % MELANIN |
|---|---|
| Control | 100.0 |
| 0.1 mM Kojic acid | 44.5 |
| 1 mM Lipochroman-6 | 96.6 |
| 1 mM 7-methoxy-6-palmitoyl-2,2-dimethylchromane | 63.0 |

Example 8 (*Prophetic*)

Comparative Activity Assay of 7-methoxy-6-palmitoyl-2,2-dimethylchromane on Endogenous Tyrosinase Extracted from Human Melanocytes The human melanocytes are cultured in DMEM medium supplemented with 10% FBS, 1% penicillin/streptomycin and 100 nM PMA. The compound 7-methoxy-6-palmitoyl-2,2-dimethylchromane is dissolved in 1:1 DMSO:sterile water at a final concentration of 10 mM.

The endogenous tyrosine of the human melanocytes seeded at a confluence of 95% is extracted. The assay is performed after extracting and quantifying the enzymatic content. Such assay consists of incubating the tyrosinase enzyme for 30 minutes with Lipochroman-6 (1 mM), 7-methoxy-6-palmitoyl-2,2-dimethylchromane (1 mM) or with kojic acid (0.1 mM) as a comparative agent. To check the enzymatic activity after the treatment, the synthetic L-Dopa (10 mM) substrate is added, measuring absorbance at a wavelength of 475 nm one hour after having added L-Dopa. This measurement allows evaluating the melanin content produced.

Table 2 measures the percentage of melanogenesis in relation to a control sample, one hour after having added L-Dopa, for the comparative sample with kojic acid and for the samples with 7-methoxy-6-palmitoyl-2,2-dimethylchromane and with Lipochroman-6.

TABLE 2

| COMPOUND | % MELANIN |
|---|---|
| Control | 100.0 |
| 0.1 mM Kojic acid | 31.0 |
| 1 mM Lipochroman-6 | 79.8 |
| 1 mM 7-methoxy-6-palmitoyl-2,2-dimethylchromane | 57.0 |

Example 9 (*Prophetic*)

Comparative Assay of the Depigmenting Efficacy of 7-methoxy-6-palmitoyl-2,2-dimethylchromane in Human Melanocyte Cultures The human melanocytes seeded in confluence are cultured for 5 days adding fresh medium daily containing 0.1 mM of kojic acid or of 7-methoxy-6-palmitoyl-2,2-dimethylchromane. The melanin content [was] *is* seen directly by means of microscopy using a 40 magnification lens. The depigmenting efficacy [was] *is* determined by counting the number of cells containing melanin and the total number of cells, and the obtained results [were] *are* normalized in relation to the whitening efficacy of a control sample.

TABLE 3

| COMPOUND | % DEPIGMENTING EFFICACY |
|---|---|
| Control | 0.0 |
| 0.1 mM Kojic acid | 30.2 |
| 0.1 mM 7-methoxy-6-palmitoyl-2,2-dimethylchromane | 45.9 |

Example 10

Assay of the Photoprotecting Efficacy of 7-methoxy-6-palmitoyl-2,2-dimethylchromane in Human Keratinocyte Cultures The human keratinocytes were maintained in culture for 24 hours in 96 well plates to form monolayers and the cells were pre-incubated in the dark with 150 μg/mL of 7-methoxy-6-palmitoyl-2,2-dimethylchromane or saline phosphate buffer (control) for one hour at 37° C. and humidified air with 5% $CO_2$. The cells were then irradiated with a solar simulation lamp with an energy of 37 J/cm$^2$ at room temperature for 150 minutes. A control plate was maintained in the dark for the same time at room temperature. The medium of the cells was replaced after the irradiation period with fresh medium and the cells were incubated for 24 additional hours. The cell viability was determined by means of the Neutral Red dye, measuring the optical density at 540 nm in a spectrophotometer.

The photoprotecting efficacy was determined by comparing the viability obtained in the cells treated with 7-methoxy-6-palmitoyl-2,2-dimethylchromane in relation to the response of the irradiated and non-irradiated control cells.

TABLE 4

| TREATMENT | CELL VIABILITY | PHOTOPROTECTTNG EFFICACY |
|---|---|---|
| Control | 100% | — |
| Irradiated control | 13.8% | — |
| 150 μg/mL 7-methoxy-6-palmitoyl-2,2-dimethylchromane | 49.1% | 254.9% |

The invention claimed is:

1. A compound of general formula (I)

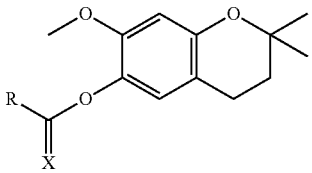

or its cosmetically or pharmaceutically acceptable [salts] *salt*, wherein

R is a linear or branched, saturated or unsaturated aliphatic group containing 2 to 23 carbon atoms[, or a cyclic group,] and which can contain substituents selected from the group consisting of hydroxy, alkoxy, amino, carboxyl, cyano, nitro, alkylsulfonyl or halogen atoms; and X is selected from the group consisting of O and S.

2. A The compound according to claim 1, wherein X is O.

3. The [compound] *composition* according to claim [1] *8*, wherein R is a saturated or unsaturated aliphatic group, containing 2 to 23 carbon atoms.

4. The compound according to claim [2 or 3] *1*, wherein

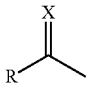

is selected from the group consisting of tert-butanoyl, hexanoyl, 2-methylhexanoyl, octanoyl, decanoyl, lauroyl, myristoyl, palmitoyl, stearoyl, oleoyl and linoleoyl.

5. The [compound] *composition* according to claim [1] *8*, wherein R is an alicyclic cyclic group, an aromatic cyclic group or a heterocyclic cyclic group.

6. The [compound] *composition* according to [claims 2 or 5] *claim 8*, wherein

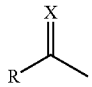

is selected from the group consisting of [—CO—(CH2)0_6_phenyl] —*CO*—$(CH_2)_{0\text{-}6}$-*phenyl*, [—CO—(CH2)0_6_(1-naphthyl)] —*CO*—$(CH_2)_{0\text{-}6}$-(*1-naphthyl*), [—CO—(CH2)0_6_(2-naphthyl)] —*CO*—$(CH_2)_{0\text{-}6}$-(*2-naphthyl*), [—CO—(CH2)0_6_—CH(phenyl)2] —*CO*—$(CH_2)_{0\text{-}6}$-*CH*$(phenyl)_2$, —CO-(2-fluorophenyl), —CO—cyclohexyl, [c~-lipoyl] α-*lipoyl*, L-prolyl, D-prolyl, biotinyl —CO-(4-imidazolyl), —CO-(2-pyridyl), —CO-(2-thienyl), —CO-(2-furyl) and —CO-(3-furyl).

7. A process of obtaining a compound of general formula (I) or its cosmetically or pharmaceutically acceptable [salts] *salt* according to claim 1, wherein 6-hydroxy-7-methoxy-2,2-dimethylchromane is reacted with the compound of general formula (II)

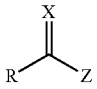

wherein X is selected from the group consisting of O and S;

R is a linear or branched, saturated or unsaturated aliphatic group with from 2 to 23 carbon atoms[, or a cyclic group,] and which can contain substituents selected from the group consisting of hydroxy, alkoxy, amino, carboxyl, cyano, nitro, alkylsulfonyl and halogen atoms[, or a cyclic group]; and Z is a free OH group[, a reactive derivative thereof] or a halogen.

8. A cosmetic or pharmaceutical composition comprising*:* a cosmetically or pharmaceutically effective amount of at least one compound of general formula (I)

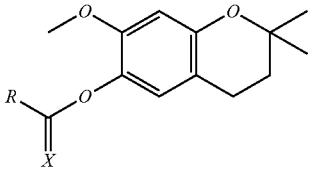

or its cosmetically or pharmaceutically acceptable [salts according to claim 1, comprises] *salt, wherein*

*R is a linear or branched, saturated or unsaturated aliphatic group containing 2 to 23 carbon atoms, or a cyclic group, and which can contain substituents selected from the group consisting of hydroxy, alkoxy, amino, carboxyl, cyano, nitro, alkylsulfonyl or halogen atoms; and*

*X is selected from the group consisting of O and S or its cosmetically or pharmaceutically acceptable salt; and* at least one cosmetically or pharmaceutically acceptable excipient or adjuvant*, and*

*wherein the compound of general formula (I) or its cosmetically or pharmaceutically acceptable salt is present at from 0.00000001% to 20% by weight of the composition.*

9. The cosmetic or pharmaceutical composition according to claim 8, wherein the compound of general formula (I) or its cosmetically or pharmaceutically acceptable [salts] *salt* are incorporated in a cosmetically or pharmaceutically acceptable sustained release system or carrier selected from the group consisting of liposomes, millicapsules, microcapsules, nanocapsules, sponges, vesicles, micelles, millispheres, microspheres, nanospheres, lipospheres, microemulsions, nanoemulsions, milliparticles, microparticles and nanoparticles.

10. The cosmetic or pharmaceutical composition according to claim 8, wherein the compound of general formula (I) or its cosmetically or pharmaceutically acceptable [salts] *salt* are adsorbed on a cosmetically or pharmaceutically acceptable organic polymer or solid mineral support selected from the group consisting of talc, bentonite, silica, starch and maltodextrin.

11. The cosmetic or pharmaceutical composition according to claim 8, wherein it has a formulation selected from the group consisting of creams, oil and/or silicone in water emulsions, water in oil and/or silicone emulsions, water/oil or silicone/water type emulsions, oil or silicone/water/oil or silicone type emulsions, oils, milks, balsams, foams, lotions, hydroalcoholic solutions, gels, liniments, serums, soaps, shampoos, ointments, mousses, salves, powders, bars, pencils, sprays or aerosols, capsules, [including gelatin capsules,] tablets, [including sugar-coated tablets,] powders, granulated forms, chewing gums, solutions, suspensions, emulsions, syrups, jellies and gelatin.

12. The cosmetic or pharmaceutical composition according to claim 8, wherein the compound of general formula (I) or its cosmetically or pharmaceutically acceptable [salts] *salt* are incorporated in solid accessories selected from the group consisting of towelettes, hydrogels, adhesive patches, non-adhesive patches and face masks.

13. The cosmetic or pharmaceutical composition according to claim 8, wherein the compound of general formula (I) or its cosmetically or pharmaceutically acceptable [salts] *salt* are incorporated in makeup products selected from the group consisting of under eye concealers, makeup bases, makeup removal lotions and makeup removal milks.

14. The cosmetic or pharmaceutical composition according to claim 8, wherein the compound of general formula (I) or its cosmetically or pharmaceutically acceptable [salts] *salt* are incorporated in fabrics.

15. The cosmetic or pharmaceutical composition according to claim 8, wherein it further comprises an additional cosmetically or pharmaceutically effective amount of at least one active agent selected from the group consisting of a depigmenting or whitening agent, an anti-stretch mark agent, an anti-wrinkle agent, an antioxidant agent, an anti-glycation agent, an NO-synthase inhibitor, an anti-ageing agent, an agent capable of reducing or eliminating bags under the eyes, an exfoliating agent, emulsifying agents, emollients, organic solvents, liquid propellants, skin conditioners, wetting agents, moisture retaining substances, alpha hydroxy acids, moisturizers, vitamins, pigments or colorants, dyes, gelling polymers, thickeners, surfactants, softeners, an agent stimulating dermal or epidermal molecule synthesis and/or for preventing or inhibiting their degradation, an agent stimulating collagen synthesis, an agent stimulating decorin synthesis, an agent stimulating elastin synthesis, an agent stimulating laminin synthesis, an agent inhibiting collagen degradation, an agent inhibiting elastin degradation, an agent stimulating fibroblast and/or keratinocyte proliferation or for stimulating keratinocyte differentiation, agents stimulating lipid synthesis and synthesis of components of the stratum corneum, agents stimulating glycosaminoglycan synthesis, DNA repair agents, DNA protecting agents, agents stimulating defensin synthesis, agents stimulating chaperone synthesis, anti-pruritus agents, agents for treating sensitive skin, astringent agents, sebum production regulating agents, anti-cellulite agents, agents stimulating lipolysis, agents intended to improve the dermal-epidermal junction, a dermorelaxing agent, a [reaffirming] *firming* agent, an anti-atmospheric contamination and/or free radical scavenger, an agent acting on capillary circulation and/or microcirculation, a calming agent, an anti-inflammatory agent, an antimicrobial agent, an antifungal agent, bactericides, an agent acting on cell metabolism, a chelating agent and/or an organic or mineral photoprotective agent active against ultraviolet A and/or B rays, and mixtures thereof.

16. The cosmetic or pharmaceutical composition according to claim 15, wherein the active agent is a desquamating agent selected from the group consisting of alpha hydroxy acids, beta hydroxy acids, urea [and derivatives thereof], gentisic acid, cinnamic acid, jasmonic acid [and derivatives thereof], oligofucoses, resveratrol, N-acetylglucosamine, Saphorajaponica extract, detergents and enzymes.

17. The cosmetic or pharmaceutical composition according to claim 15, wherein the active agent is an organic or mineral photoprotective agent active against ultraviolet A and/or B rays.

18. The cosmetic or pharmaceutical composition according to claim 15, wherein the active agent is a whitening or depigmenting agent selected from the group consisting of 6-hydroxy-7- methoxy-2,2-dimethylchromane, arbutin and isomers thereof, kojic acid [and derivatives thereof], vitamin C [and derivatives thereof including], 6-O-palmitoylascorbic acid, magnesium salt of ascorbic acid-2-phosphate (MAP), sodium salt of ascorbic acid-2-phosphate (NAP), ascorbyl glucoside and ascorbyl tetraisopalmitate (VCIP), retinol [and derivatives thereof including], tretinoin and isotretinoin, idebenone, hydroxybenzoic acid [and derivatives thereof], flavonoids, soy extract, yeast extract, lemon extract, orange extract, ginkgo extract, cucumber extract, geranium extract, bearberry extract, carob bean extract, cinnamon extract, marjoram extract, rosemary extract, clove extract, soluble licorice extract, blackberry leaf extract, niacinamide, liquiritin, resorcinol [and derivatives thereof], hydroquinone, α-tocopherol, Y-tocopherol, azelaic acid, resveratrol, mercury salts, linoleic acid, α-lipoic acid, dihydrolipoic acid, alpha hydroxy acids, beta hydroxy acids, ellagic acid, ferulic acid, cinnamic acid, oleanolic acid, aloesin [and derivatives thereof], dithiaoctanediol, gluconic acid, beta-carotene, serine protease inhibitors, [including tryptase, trypsin and PAR-2 inhibitors,] diacetylboldine, undecylenoyl phenylalanine, nonapeptide-1, amino ethyl phosphoric acid, Achillea millefolium extract, Alchemilla vulgaris extract, Aloe vera extract, Azadirachta indica extract, Arctostaphylos uva ursi leaf extract, Osmunda japonica extract, Artocarpus incisus extract, Bidens pylosa extract, Brassica napus extract, Broussonetia papyrifera extract, Chlorella vulgaris extract, Cimicifiiga racemosa extract, Emblica officinalis extract, Glycyrrhiza glabra extract, extract of Glycyrrhiza uralensis, Ilex purpurea extract, Ligusticum lucidum extract, Ligusticum wallichii extract, Malva sylvestris extract, Melissa officinalis leaf extract, Mentha piperita leaf extract, Mitracarpus scaber extract, Morinda citrifolia extract, Morus alba extract, Morus bombycis extract, Naringi crenulata extract, Pisum sativum extract, Primula veris extract, Prunus domesticus extract, Pseudostellariae radix extract, Rumex crispus extract, Rumex occidentalis extract, Sapindus mukurossi extract, Saxifraga sarmentosa extract, Scutellaria galericulata extract, Sedum sarmentosum Bunge extract, Stellaria medica extract, Triticum Vulgare extract, Uva ursi extract, Veronica officinalis extract, Withania somnifera extract and leukocyte extract.

19. A method for treating, caring for, or cleaning skin, hair or nails in a subject in need of such treatment comprising applying to said subject a cosmetic or pharmaceutical composition comprising a compound of general formula (I)

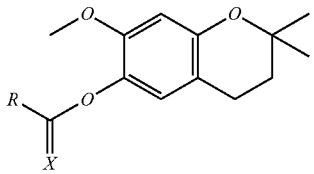

or its cosmetically or pharmaceutically acceptable [salts according to claim 1] *salt,*

*wherein*

*R is a linear or branched, saturated or unsaturated aliphatic group containing 2 to 23 carbon atoms, or a cyclic group, and which can contain substituents selected from the group consisting of hydroxy, alkoxy, amino, carboxyl, cyano, nitro, alkylsulfonyl or halogen atoms; and*

*X is selected from the group consisting of O and S.*

20. A method of regulating the pigmentation of the skin, hair or nails in a subject in need of such regulating, comprising applying to said subject a cosmetic or pharmaceutical composition [comprising a compound of general formula (I) or its cosmetically or pharmaceutically acceptable salts] according to claim [1] *8*.

21. A method for whitening or lightening the skin in a subject in need of such whitening or lightening comprising applying to said subject a cosmetic or pharmaceutical composition [comprising a compound of general formula (I) or its cosmetically or pharmaceutically acceptable salts] according to claim [1] *8*.

22. A method for treating skin pigmentation disorders or pathologies in a subject in need of such treatment, comprising applying to said subject a cosmetic or pharmaceutical composition [comprising a compound of general formula (I) or its cosmetically or pharmaceutically acceptable salts] according to claim [1] *8*.

23. A method for reducing or delaying the signs of aging or photoaging in a subject in need of such delaying or reducing, comprising applying to said subject a cosmetic or pharmaceutical composition [comprising a compound of general formula (I) or its cosmetically or pharmaceutically acceptable salts] according to claim [1] *8*.

24. A method for photoprotecting skin, hair or nails in a subject in need of such photoprotecting, comprising applying to said subject a cosmetic or pharmaceutical composition comprising a compound of general formula (I) or its cosmetically or pharmaceutically acceptable salts according to claim 1.

25. The method according to any one of claims 19-24 wherein said applying comprises topical or transdermal application of said composition.

*26. The compound according to claim 1, wherein R is* $CH_3(CH_2)_{14}$—.

*27. The compound according to claim 1, wherein the compound is 7-methoxy-6-palmitoyl-2,2-dimethylchromane.*

*28. A compound of general formula (I)*

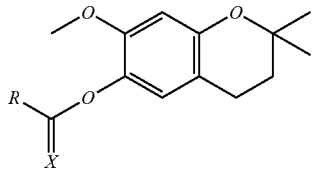

*or its cosmetically or pharmaceutically acceptable salt, wherein*

*R is*

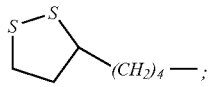

*and*

*X is selected from the group consisting of O and S.*

*29. The cosmetic or pharmaceutical composition according to claim 8, wherein the compound of general formula (I) or its cosmetically or pharmaceutically acceptable salt is present at between 0.00001% and 10% by weight of the composition.*

*30. The composition according to claim 3, wherein*

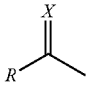

*is selected from the group consisting of tert-butanoyl, hexanoyl, 2-methylhexanoyl, octanoyl, decanoyl, lauroyl, myristoyl, palmitoyl, stearoyl, oleoyl and linoleoyl.*

* * * * *